(12) United States Patent
Abe

(10) Patent No.: US 9,353,071 B2
(45) Date of Patent: May 31, 2016

(54) METHOD FOR MANUFACTURING ISOTHIAZOLE COMPOUND

(71) Applicant: IHARA CHEMICAL INDUSTRY CO., LTD., Tokyo (JP)

(72) Inventor: Takashi Abe, Shizuoka (JP)

(73) Assignee: IHARA CHEMICAL INDUSTRY CO., LTD., Tokyo (JP)

( * ) Notice: Subject to any disclaimer, the term of this patent is extended or adjusted under 35 U.S.C. 154(b) by 0 days.

(21) Appl. No.: 14/432,589

(22) PCT Filed: Oct. 4, 2013

(86) PCT No.: PCT/JP2013/005925
§ 371 (c)(1),
(2) Date: Mar. 31, 2015

(87) PCT Pub. No.: WO2014/054294
PCT Pub. Date: Apr. 10, 2014

(65) Prior Publication Data
US 2015/0291540 A1    Oct. 15, 2015

(30) Foreign Application Priority Data
Oct. 5, 2012   (JP) ................................. 2012-223321

(51) Int. Cl.
C07D 275/03      (2006.01)
C07D 275/02      (2006.01)

(52) U.S. Cl.
CPC ............ *C07D 275/03* (2013.01); *C07D 275/02* (2013.01)

(58) Field of Classification Search
CPC combination set(s) only.
See application file for complete search history.

(56) References Cited

U.S. PATENT DOCUMENTS

| | | | |
|---|---|---|---|
| 3,341,547 A | 9/1967 | Mailey | |
| 4,132,676 A * | 1/1979 | Virgilio | C11B 9/0096 424/64 |
| 6,191,155 B1 * | 2/2001 | Assmann | A01N 43/80 514/236.8 |
| 6,706,748 B2 * | 3/2004 | Kitagawa | A01N 43/80 514/372 |
| 8,563,745 B2 * | 10/2013 | Nakamura | C07D 275/02 548/214 |

FOREIGN PATENT DOCUMENTS

| | | |
|---|---|---|
| DE | 2231097 A | 1/1974 |
| DE | 2231098 A1 | 1/1974 |
| JP | H05-59024 A | 3/1993 |
| JP | 4088036 B2 | 5/2008 |
| JP | 2010-260805 A | 11/2010 |
| WO | 2010/126170 A1 | 11/2010 |

OTHER PUBLICATIONS

International Preliminary Report on Patentability (IPRP) dated Apr. 7, 2015, for PCT/JP2013/005925, and English translation thereof.
International Search Report (ISR) dated Dec. 3, 2013, for PCT/JP2013/005925, and English translation thereof.

* cited by examiner

*Primary Examiner* — Nyeemah A Grazier
(74) *Attorney, Agent, or Firm* — Bacon & Thomas, PLLC

(57) ABSTRACT

An industrially preferred process for producing an isothiazole compound, particularly 3,4-dichloro-5-cyanoisothiazole, provides a safer industrial production process by avoiding the simultaneous use of an aprotic polar solvent such as N,N-dimethylformamide and chlorine. In addition, a production process which is economically preferred because an aprotic polar solvent, which is highly likely to become a part of waste, is not used.

A process for producing an isothiazole compound represented by a general formula (3), wherein R is a cyano group or the like; and X is a chlorine atom or the like, which comprises heating a nitrile compound represented by a general formula (1), wherein R is as defined above, and sulfur, and then carrying out a reaction between the nitrile compound represented by the general formula (1), the sulfur and a halogen represented by a general formula (2), wherein X is as defined above.

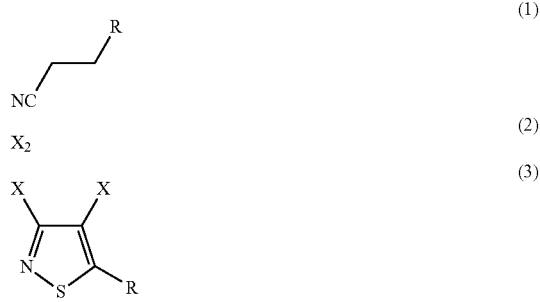

30 Claims, No Drawings

METHOD FOR MANUFACTURING ISOTHIAZOLE COMPOUND

The present invention relates to a process for producing an isothiazole compound. Isothiazole compounds are useful, for example, as intermediates for the synthesis of various organic compounds (e.g., biologically active organic compounds such as pharmaceuticals and agricultural chemicals, functional pigments, electronic materials, etc.) because of their structure of isothiazole.

BACKGROUND ART

As described above, isothiazole compounds are widely known as intermediates for pharmaceuticals and intermediates for agricultural chemicals, and intermediates for functional pigments, electronic materials, etc. Therefore, as disclosed in Non-Patent Documents 1 and 2, various studies have heretofore been made on processes for producing isothiazole compounds.

Among isothiazole compounds, 3,4-dichloro-5-cyanoisothiazole, which can easily be subjected to the conversion of a functional group thereof, is known as an intermediate for pharmaceuticals and an intermediate for agricultural chemicals. In addition, as disclosed in Patent Documents 4 and 5, this compound is in fact used as an important intermediate for agricultural chemicals.

However, it has been difficult for the production processes disclosed in Non-Patent Documents 1 and 2 to produce 3,4-dichloro-5-cyanoisothiazole, which is useful as an important intermediate for agricultural chemicals.

That is, a process using carbon disulfide ($CS_2$), sodium cyanide (NaCN) and chlorine ($Cl_2$) has heretofore been known as a process for producing 3,4-dichloro-5-cyanoisothiazole (see Patent Document 1). However, this process has a drawback that carbon disulfide, which is a special inflammable material, is used as a raw material to be used therein. Moreover, this process also has a drawback that sodium cyanide, which is a toxic material, is used therein. Furthermore, in this process, chlorine is introduced into a reactor containing therein N,N-dimethylformamide (DMF) as a solvent with heating. However, it is well known to a person skilled in the art that when N,N-dimethylformamide and chlorine are used simultaneously, there is a possibility of the runaway of the reaction or an explosion. For these reasons, it is considered that the implementation of this process requires most careful attention and adequate measures in order to maintain safety. In addition, there is a possibility that this process cannot ensure the safety of a production plant because there is a possibility that the runaway of the reaction and an explosion occur in some cases as described above. That is, this process using N,N-dimethylformamide and chlorine at the same time is not preferred for industrial manufacture because there is concern for lack of safety.

As another process for producing 3,4-dichloro-5-cyanoisothiazole, a process using trichloroacetonitrile and sulfur is known (see Patent Document 2). However, this process has the drawback of requiring the reaction at a high temperature of 200° C. to 300° C. as described in Examples therein. In addition, this process has the drawback of requiring the use of a special raw material such as trichloroacetonitrile.

Furthermore, a process using dichlorofumaronitrile and sulfur is known (see Patent Document 3). However, this process also has the drawback of requiring the reaction at a high temperature of 230° C. to 300° C. in Examples therein. In addition, this process also has the drawback of requiring the use of a special raw material such as dichlorofumaronitrile.

As still another production process, a process of reacting fumaronitrile, maleonitrile or a chlorine-substituted compound thereof, or a mixture of these compounds with sulfur chloride in an aprotic polar solvent is known (see Patent Document 6). Fumaronitrile, maleonitrile and a chlorine-substituted compound thereof, or a mixture of these compounds, which is/are used in this process, can be produced from succinonitrile (see Examples 7 and 8 of Patent Document 6). However, it is desired that the production process described in Patent Document 6 is further improved in that this process requires two steps from succinonitrile.

In addition, it is considered that fumaronitrile, maleonitrile or a chlorine-substituted compound thereof has an industrially significant sublimation property. Compounds having a sublimation property generally have the potential of causing clogging of a reflux condenser or a pipeline in a plant by sublimation thereof. For this reason, the process described in Patent Document 6 has the drawback of having the possibility of requiring attention and measures in operations in its industrial implementation.

Besides, this process essentially requires an aprotic polar solvent such as N,N-dimethylformamide. And the recycle of the aprotic polar solvent is accompanied by difficulty because of working-up using water. Therefore, there is a drawback that it is highly possible that the used aprotic polar solvent becomes a part of waste. In addition, in this process, there is an example in which N,N-dimethylformamide and sulfur chloride, which is a chlorine compound, are used simultaneously. Therefore, there is a possibility that this process requires attention and measures with the view of preparing for any situation. Therefore, there is still room for improvement in this process.

Meanwhile, as a production process of 3,4-dichloro-5-cyanoisothiazole, a process using succinonitrile, sulfur and chlorine is known (see Patent Document 7). However, this process also requires N,N-dimethylformamide as a solvent. That is, since N,N-dimethylformamide and chlorine are used simultaneously, there is a possibility of the runaway of the reaction and an explosion. For this reason, it is considered that the implementation of this process also requires most careful attention and adequate measures in order to maintain safety. In addition, there is a possibility that this process cannot ensure the safety of a production plant because there is a possibility that the runaway of the reaction and an explosion occur in some cases as described above. That is, this process using N,N-dimethylformamide and chlorine at the same time is not preferred for industrial manufacture because there is concern for lack of safety.

Besides, the process described in Patent Document 7 essentially requires an aprotic polar solvent such as N,N-dimethylformamide. And the recycle of the aprotic polar solvent is accompanied by difficulty because of working-up using water. Therefore, there is a drawback that it is highly possible that the used aprotic polar solvent becomes a part of waste. That is to say, there is still room for improvement in this process.

Patent Document 1: U.S. Pat. No. 3,341,547 A
Patent Document 2: DE 2231097 A (DT 2231097)
Patent Document 3: DE 2231098 A (DT 2231098)
Patent Document 4: Japanese Patent Application Laid-Open No. Hei-5-59024 (JP-A-1993-59024)
Patent Document 5: Japanese Patent No. 4088036
Patent Document 6: International Publication No. WO2010/126170

Patent Document 7: Japanese Patent Application Laid-Open No. 2010-260805 (JP 2010-260805 A)

Non-Patent Document

Non-Patent Document 1: Tetrahedron Lett., No. 42, 1970, pp. 3719-3722
Non-Patent Document 2: Chem. Commun., 2002, pp. 1872-1873

SUMMARY OF INVENTION

An object of the present invention is to provide a safer industrial process for producing an isothiazole compound, particularly 3,4-dichloro-5-cyanoisothiazole, by avoiding the simultaneous use of an aprotic polar solvent such as N,N-dimethylformamide and chlorine.

Another object of the present invention is to provide a process for producing an isothiazole compound, particularly 3,4-dichloro-5-cyanoisothiazole, which is economically preferred because an aprotic polar solvent such as N,N-dimethylformamide, which is highly likely to become a part of waste, is not used.

Still another object of the present invention is to provide a process for producing an isothiazole compound, particularly 3,4-dichloro-5-cyanoisothiazole, which process does not substantially use a raw material, which may require attention and measures, or a special raw material. An example of the raw material which may require attention and measures is an inorganic cyanide having extremely high toxicity, which is a source for hydrocyanic acid gas and cyanide ions. In addition, another example of the raw material which may require attention and measures is a special inflammable material. In addition, still another example of the raw material which may require attention and measures is an organic compound having an industrially significant sublimation property.

Still another object of the present invention is to provide a process which can produce an isothiazole compound, particularly 3,4-dichloro-5-cyanoisothiazole, using easily available and inexpensive raw materials.

Still another object of the present invention is to provide a process for producing an isothiazole compound, particularly 3,4-dichloro-5-cyanoisothiazole, which process is suitable for industrialization because of a simple operation.

For example, the production process described in the above Patent Document 6 requires two steps from succinonitrile in order to produce 3,4-dichloro-5-cyanoisothiazole. However, to provide a process which can produce, for example, 3,4-dichloro-5-cyanoisothiazole, in a simple manner in only one step from succinonitrile is one of the objects of the present invention.

In short, an object of the present invention is to provide an industrially preferred process for producing an isothiazole compound, particularly 3,4-dichloro-5-cyanoisothiazole.

In view of the circumstances as described above, the present inventor has earnestly studied processes for producing an isothiazole compound represented by a general formula (3) described later. As a result, the present inventor has unexpectedly found that the isothiazole compound represented by the general formula (3) described later can be produced by heating a nitrile compound represented by a general formula (1) described later and sulfur, and then carrying out the reaction between the nitrile compound represented by the general formula (1) described later, the sulfur and a halogen represented by a general formula (2) described later. Particularly, the present inventor has unexpectedly found that 3,4-dichloro-5-cyanoisothiazole represented by a formula (6) described later can be produced by heating succinonitrile represented by a formula (4) described later and sulfur, and then carrying out the reaction between the succinonitrile represented by the formula (4) described later, the sulfur and chlorine represented by a formula (5). Based on these findings, the present inventor has completed the present invention. That is, the present invention is as follows:

[1] A process for producing an isothiazole compound represented by a general formula (3):

[Chemical Formula 3]

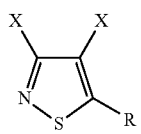

(3)

(wherein R is a cyano group, a carboxy group or an alkoxycarbonyl group; and X is a fluorine atom, a chlorine atom, a bromine atom or an iodine atom)

which comprises carrying out a reaction between a nitrile compound represented by a general formula (1):

[Chemical Formula 1]

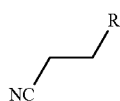

(1)

(wherein R is as defined above), sulfur and a halogen represented by a general formula (2):

[Chemical Formula 2]

$X_2$ (2)

(wherein X is as defined above).

[2] The process according to [1], wherein the nitrile compound represented by the general formula (1) and the sulfur are heated, and then the reaction between the nitrile compound represented by the general formula (1), the sulfur and the halogen represented by the general formula (2) is carried out.

[3] The process according to [1], wherein the nitrile compound represented by the general formula (1) and the sulfur are heated until at least the nitrile compound represented by the general formula (1) is melted

[4] The process according to [1], wherein the nitrile compound represented by the general formula (1) and the sulfur are heated until at least the nitrile compound represented by the general formula (1) and a part of the sulfur are melted.

[5] The process according to [1], wherein the nitrile compound represented by the general formula (1) and the sulfur are heated until the nitrile compound represented by the general formula (1) and the sulfur are melted.

[6] The process according to any one of [1] to [5], wherein the nitrile compound represented by the general formula (1) and the sulfur are heated to 70° C. or more.

[7] The process according to any one of [1] to [5], wherein the nitrile compound represented by the general formula (1) and the sulfur are heated to 90° C. or more.

[8] The process according to any one of [1] to [5], wherein the nitrile compound represented by the general formula (1) and the sulfur are heated to a temperature in the range of 50 to 200° C.

[9] The process according to any one of [1] to [5], wherein the nitrile compound represented by the general formula (1) and the sulfur are heated to a temperature in the range of 70 to 180° C.

[10] The process according to any one of [1] to [5], wherein the nitrile compound represented by the general formula (1) and the sulfur are heated to a temperature in the range of 90 to 150° C.

[11] The process according to any one of [1] to [10], wherein the reaction between the nitrile compound represented by the general formula (1), the sulfur and the halogen represented by the general formula (2) is carried out at 70° C. or more.

[12] The process according to any one of [1] to [10], wherein the reaction between the nitrile compound represented by the general formula (1), the sulfur and the halogen represented by the general formula (2) is carried out at 90° C. or more.

[13] The process according to any one of [1] to [10], wherein the reaction between the nitrile compound represented by the general formula (1), the sulfur and the halogen represented by the general formula (2) is carried out at a temperature in the range of 50 to 200° C.

[14] The process according to any one of [1] to [10], wherein the reaction between the nitrile compound represented by the general formula (1), the sulfur and the halogen represented by the general formula (2) is carried out at a temperature in the range of 70 to 180° C.

[15] The process according to any one of [1] to [10], wherein the reaction between the nitrile compound represented by the general formula (1), the sulfur and the halogen represented by the general formula (2) is carried out at a temperature in the range of 90 to 150° C.

[16] The process according to any one of [1] to [15], wherein the reaction between the nitrile compound represented by the general formula (1), the sulfur and the halogen represented by the general formula (2) is carried out for 15 hours or more.

[17] The process according to any one of [1] to [15], wherein the reaction between the nitrile compound represented by the general formula (1), the sulfur and the halogen represented by the general formula (2) is carried out for 20 hours or more.

[18] The process according to any one of [1] to [15], wherein the reaction between the nitrile compound represented by the general formula (1), the sulfur and the halogen represented by the general formula (2) is carried out for a time period in the range of 15 to 75 hours.

[19] The process according to any one of [1] to [15], wherein the reaction between the nitrile compound represented by the general formula (1), the sulfur and the halogen represented by the general formula (2) is carried out for a time period in the range of 20 to 50 hours.

[20] The process according to any one of [1] to [19], wherein the reaction between the nitrile compound represented by the general formula (1), the sulfur and the halogen represented by the general formula (2) is carried out by charging the nitrile compound represented by the general formula (1) and the sulfur, and then introducing the halogen represented by the general formula (2) therein.

[21] The process according to any one of [1] to [20], wherein the reaction between the nitrile compound represented by the general formula (1), the sulfur and the halogen represented by the general formula (2) is carried out by introducing the halogen represented by the general formula (2) into the nitrile compound represented by the general formula (1) and the sulfur.

[22] The process according to any one of [1] or [6] to [21], wherein the nitrile compound represented by the general formula (1) is in a molten state.

[23] The process according to any one of [1] or [6] to [21], wherein the sulfur is in a molten state.

[24] The process according to any one of [1] or [6] to [21], wherein the nitrile compound represented by the general formula (1) is in a molten state, and the sulfur is in a molten state.

[25] The process according to any one of [20] to [24], wherein the introduction of the halogen represented by the general formula (2) is carried out at 70° C. or more.

[26] The process according to any one of [20] to [24], wherein the introduction of the halogen represented by the general formula (2) is carried out at 90° C. or more.

[27] The process according to any one of [20] to [24], wherein the introduction of the halogen represented by the general formula (2) is carried out at a temperature in the range of 50 to 200° C.

[28] The process according to any one of [20] to [24], wherein the introduction of the halogen represented by the general formula (2) is carried out at a temperature in the range of 70 to 180° C.

[29] The process according to any one of [20] to [24], wherein the introduction of the halogen represented by the general formula (2) is carried out at a temperature in the range of 90 to 150° C.

[30] The process according to any one of [20] to [29], wherein the introduction of the halogen represented by the general formula (2) is carried out for 15 hours or more.

[31] The process according to any one of [20] to [29], wherein the introduction of the halogen represented by the general formula (2) is carried out for 20 hours or more.

[32] The process according to any one of [20] to [29], wherein the introduction of the halogen represented by the general formula (2) is carried out for a time period in the range of 15 to 75 hours.

[33] The process according to any one of [20] to [29], wherein the introduction of the halogen represented by the general formula (2) is carried out for a time period in the range of 20 to 50 hours.

[34] The process according to any one of [1] to [33], wherein the reaction between the nitrile compound represented by the general formula (1), the sulfur and the halogen represented by the general formula (2) is carried out without using an aprotic polar solvent.

[35] The process according to any one of [1] to [33], wherein the reaction between the nitrile compound represented by the general formula (1), the sulfur and the halogen represented by the general formula (2) is carried out without a solvent.

[36] The process according to any one of [1] to [35], wherein an amount of sulfur used is 0.5 mol or more and 20 mol or less, as sulfur atoms, based on 1 mol of the nitrile compound represented by the general formula (1).

[37] The process according to any one of [1] to [35], wherein an amount of sulfur used is 0.9 mol or more and 12 mol or less, as sulfur atoms, based on 1 mol of the nitrile compound represented by the general formula (1).

[38] The process according to any one of [1] to [35], wherein an amount of sulfur used is 0.9 mol or more and 4 mol or less, as sulfur atoms, based on 1 mol of the nitrile compound represented by the general formula (1).

[39] The process according to any one of [1] to [35], wherein an amount of sulfur used is 1 mol or more and 20 mol or less, as sulfur atoms, based on 1 mol of the nitrile compound represented by the general formula (1).

[40] The process according to any one of [1] to [35], wherein an amount of sulfur used is 1 mol or more and 12 mol or less, as sulfur atoms, based on 1 mol of the nitrile compound represented by the general formula (1).

[41] The process according to any one of [1] to [35], wherein an amount of sulfur used is 1 mol or more and 4 mol or less, as sulfur atoms, based on 1 mol of the nitrile compound represented by the general formula (1).

[42] The process according to any one of [1] to [35], wherein an amount of sulfur used is less than 2 mol, as sulfur atoms, based on 1 mol of the nitrile compound represented by the general formula (1).

[43] The process according to any one of [1] to [35], wherein an amount of sulfur used is 1 mol or more and less than 2 mol, as sulfur atoms, based on 1 mol of the nitrile compound represented by the general formula (1).

[44] The process according to any one of [1] to [35], wherein an amount of sulfur used is 2 mol or more and 10 mol or less, as sulfur atoms, based on 1 mol of the nitrile compound represented by the general formula (1).

[45] The process according to any one of [1] to [35], wherein an amount of sulfur used is 2 mol or more and 4 mol or less, as sulfur atoms, based on 1 mol of the nitrile compound represented by the general formula (1).

[46] The process according to any one of [1] to [45], wherein an amount of the halogen represented by the general formula (2) used is 2 mol or more and 20 mol or less based on 1 mol of the nitrile compound represented by the general formula (1).

[47] The process according to any one of [1] to [45], wherein an amount of the halogen represented by the general formula (2) used is 2 mol or more and 10 mol or less based on 1 mol of the nitrile compound represented by the general formula (1).

[48] The process according to any one of [1] to [45], wherein an amount of the halogen represented by the general formula (2) used is 2 mol or more and 5 mol or less based on 1 mol of the nitrile compound represented by the general formula (1).

[49] The process according to any one of [1] to [48], wherein R in the general formula (1) is a cyano group.

[50] The process according to any one of [1] to [49], wherein X in the general formula (2) is a chlorine atom or a bromine atom.

[51] The process according to any one of [1] to [49], wherein X in the general formula (2) is a chlorine atom.

The present invention provides a novel industrial process for producing an isothiazole compound, particularly 3,4-dichloro-5-cyanoisothiazole.

According to the present invention, a safer process for producing an isothiazole compound, particularly 3,4-dichloro-5-cyanoisothiazole, is provided by avoiding the simultaneous use of an aprotic polar solvent such as N,N-dimethylformamide and chlorine. That is, according to the present invention, a process which does not require special attention or special measures in order to maintain safety is provided by not using an aprotic polar solvent such as N,N-dimethylformamide as a solvent.

Avoiding the use of an aprotic polar solvent such as N,N-dimethylformamide means significantly improved safety in the process of the present invention, i.e., the advantage of the process of the present invention, compared with prior art. In other words, it substantially reduces the risks of dangerous decomposition and the like during industrial manufacture. Therefore, the process of the present invention is safely applicable to a pilot plant or production on a larger scale such as industrial manufacture.

In addition, according to the process of the present invention, the target isothiazole compound, particularly 3,4-dichloro-5-cyanoisothiazole, can be produced without using a reaction solvent. Therefore, the process of the present invention is economically preferred compared with prior art. Particularly, with respect to an aprotic polar solvent such as N,N-dimethylformamide, recycle is accompanied by difficulty because of working-up using water. Therefore, it is highly possible that the aprotic polar solvent becomes a part of waste. However, in the process of the present invention, the target compound can be produced without using an aprotic polar solvent. Therefore, the process of the present invention can reduce waste. That is, the process of the present invention can reduce the environmental load.

Furthermore, according to the process of the present invention, the isothiazole compound, particularly 3,4-dichloro-5-cyanoisothiazole, can be produced without substantially using a raw material, which may require attention and measures, or a special raw material. An example of the raw material which may require attention and measures is an inorganic cyanide having extremely high toxicity, which is a source for hydrocyanic acid gas and cyanide ions. In addition, another example of the raw material which may require attention and measures is a special inflammable material. In addition, still another example of the raw material which may require attention and measures is an organic compound having an industrially significant sublimation property.

Besides, according to the process of the present invention, the target isothiazole compound can be produced by a simple operation in only one step from the nitrile compound as a starting material, by simultaneously reacting the nitrile compound, sulfur and the halogen. Particularly, according to the process of the present invention, the target 3,4-dichloro-5-cyanoisothiazole can be produced by a simple operation in only one step from succinonitrile as a starting material, by simultaneously reacting succinonitrile, sulfur and chlorine.

For the raw materials in the process of the present invention, all of succinonitrile among nitrile compounds, sulfur, and chlorine among halogens are raw materials which are widely used in the chemical industry and are not only easily available but inexpensive.

Furthermore, according to the process of the present invention, the isothiazole compound, particularly 3,4-dichloro-5-cyanoisothiazole, can be produced under conditions which do not require a significantly high temperature or the like and are suitable for industrialization. Specifically, for example, the process of the present invention does not require a high temperature of 200° C. or more.

In addition, as described later, the process of the present invention also provides an option in which sulfur as waste and/or tar can be suppressed or reduced, as required. That is, in the process of the present invention, it is also possible to select conditions in which the environmental load is further reduced.

Therefore, the process of the present invention can also provide a variety of preferred options in industrial implementation. Furthermore, the process of the present invention can be implemented in a simple manner and on an industrial scale without requiring a special reaction apparatus.

Therefore, the process of the present invention has high industrial use value.

DETAILED DESCRIPTION OF THE INVENTION

The present invention will be described in detail below.

The present invention specifically relates to a process for producing an isothiazole compound represented by a general formula (3):

[Chemical Formula 6]

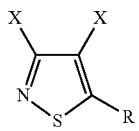
(3)

(wherein R is a cyano group, a carboxy group or an alkoxycarbonyl group; and X is a fluorine atom, a chlorine atom, a bromine atom or an iodine atom) which comprises heating a nitrile compound represented by a general formula (1):

[Chemical Formula 4]

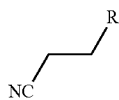
(1)

(wherein R is as defined above)
and sulfur, and then carrying out a reaction between the nitrile compound represented by the general formula (1), the sulfur and a halogen represented by a general formula (2):

[Chemical Formula 5]

$X_2$ (2)

(wherein X is as defined above).

The process of the present invention particularly relates to a process for producing 3,4-dichloro-5-cyanoisothiazole represented by a formula (6):

[Chemical Formula 9]

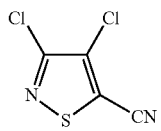
(6)

which comprises heating succinonitrile represented by a formula (4):

[Chemical Formula 7]

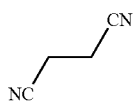
(4)

and sulfur, and then carrying out a reaction between the succinonitrile, the sulfur and chlorine represented by a formula (5):

[Chemical Formula 8]

$Cl_2$ (5)

The terms and symbols used in the present specification will be explained below.

"Ca~Cb" means that the number of carbon atoms is a to b. For example, a "C1~C4 alkyl" means that the number of carbon atoms in an alkyl is 1 to 4.

Examples of the alkyl group include a C1~C4 alkyl group. The C1~C4 alkyl means a straight chain or branched chain alkyl having 1 to 4 carbon atoms. Specific examples of the C1~C4 alkyl include methyl, ethyl, propyl, isopropyl, butyl, sec-butyl, isobutyl and tertbutyl, and preferably, methyl, ethyl, propyl and isopropyl.

Examples of the alkoxycarbonyl group include a C1~C4 alkoxycarbonyl group. The C1~C4 alkoxycarbonyl group means a (C1~C4 alkyl)-O—C(=O)— group, in which the C1~C4 alkyl group has the same meaning as described above. Specific examples of the C1~C4 alkoxycarbonyl group include methoxycarbonyl, ethoxycarbonyl, propoxycarbonyl, isopropoxycarbonyl, butoxycarbonyl, sec-butoxycarbonyl, isobutoxycarbonyl and tert-butoxycarbonyl, and preferably, methoxycarbonyl, ethoxycarbonyl, propoxycarbonyl and isopropoxycarbonyl.

(Raw Material Compounds)

The raw materials in the process of the present invention will be described.

(Nitrile Compound)

As a raw material in the process of the present invention, the nitrile compound represented by the above general formula (1) is used. In the formula (1), R is a cyano group, a carboxy group or an alkoxycarbonyl group. Therefore, examples of the nitrile compound represented by the above general formula (1) include, but are not limited to, succinonitrile, 3-cyanopropionic acid, methyl 3-cyanopropionate, ethyl 3-cyanopropionate, propyl 3-cyanopropionate, isopropyl 3-cyanopropionate and butyl 3-cyanopropionate.

From the viewpoints of availability, price, the usefulness of the product, etc., as the nitrile compound used in the process of the present invention, the succinonitrile represented by the above formula (4) is particularly preferred. The succinonitrile is currently industrially available at a relatively low cost. Furthermore, the succinonitrile is preferred as an industrial raw material also from the aspects of the handling and toxicity thereof.

(Sulfur)

The sulfur used in the process of the present invention will be described. Elemental sulfur is used in the process of the present invention. The form of the sulfur used in the process of the present invention is not particularly limited, and may be any form as long as the reaction proceeds.

The amount of sulfur used in the process of the present invention may be any amount as long as the reaction proceeds.

From the viewpoints of yield and/or the suppression of by-products, economic efficiency, etc., as the amount of sulfur used in the process of the present invention, 0.5 mol or more, preferably 0.9 mol or more, and more preferably 1 mol or more, as sulfur atoms, based on 1 mol of the nitrile compound represented by the general formula (1), can be mentioned as examples.

In addition, in a case where improvement in yield rather than the suppression of sulfur as waste and/or tar is demanded, as the amount of sulfur used in the process of the present invention, 2 mol or more, as sulfur atoms, based on 1 mol of the nitrile compound represented by the general formula (1), can be mentioned as examples.

From the viewpoints of yield and/or the suppression of by-products, economic efficiency, etc., as the amount of sulfur used in the process of the present invention, 20 mol or less, preferably 12 mol or less, more preferably 10 mol or less, and further preferably 4 mol or less, as sulfur atoms, based on 1 mol of the nitrile compound represented by the general formula (1), can be mentioned as examples.

The process described in Patent Document 1 also has a drawback that a very large amount of waste is produced as by-products. Examples of the waste include a large amount of sulfur. Furthermore, the 3,4-dichloro-5-cyanoisothiazole which is produced by the process described in Patent Document 1 contains a large amount of tar. Therefore, the process described in Patent Document 1 requires a purification step such as distillation.

In the process described in Patent Document 6, the by-production of sulfur as waste is improved compared with prior art before Patent Document 6 (e.g., the process described in Patent Document 1). However, in the process described in Patent Document 6, 1 mol of sulfur monochloride ($S_2Cl_2$) is used based on 1 mol of a raw material, i.e., fumaronitrile, maleonitrile and a chlorine-substituted compound thereof (see the Examples of Patent Document 6). Therefore, 1 mol or more of sulfur is inevitably produced as waste based on 1 mol of the raw material. Also from this viewpoint, there is room for improvement in the process described in Patent Document 6.

In a case where the suppression of sulfur as waste and/or tar rather than improvement in yield is demanded, as the amount of sulfur used in the process of the present invention, less than 2 mol, as sulfur atoms, based on 1 mol of the nitrile compound represented by the general formula (1), can be mentioned as examples.

According to the process of the present invention, when the suppression of the by-production of sulfur as waste is demanded, conditions in which the production of sulfur as a by-product can be reduced or suppressed can be selected as required (See Examples 1, 2, 6 and 8). This option, which is an advantageous effect, is obtained by using elemental sulfur. Besides, in the process of the present invention, the isothiazole compound, particularly 3,4-dichloro-5-cyanoisothiazole, containing no tar can also be produced as required. Therefore, according to the process of the present invention, conditions which do not require a purification step such as distillation can be selected as required.

Therefore, as the range of the amount of sulfur used in the process of the present invention, any appropriate combination of a lower limit and an upper limit which are described above can be mentioned as examples. The range of 0.5 mol or more and 20 mol or less, preferably 0.9 mol or more and 12 mol or less, and more preferably 0.9 mol or more and 4 mol or less, as sulfur atoms, based on 1 mol of the nitrile compound represented by the general formula (1), can be mentioned as examples. However, the amount of sulfur used in the process of the present invention can be adjusted appropriately by a person skilled in the art in accordance with the purpose and the situation.

(Halogen)

The halogen used in the process of the present invention will be described. A halogen represented by a general formula (2):

[Chemical Formula 10]

$$X_2 \qquad (2)$$

is used in the process of the present invention.

As examples of the halogen which can be used in the process of the present invention, fluorine, chlorine, bromine and iodine are mentioned.

From the viewpoints of availability, ease of handling, price, the usefulness of the product, etc., as the halogen used in the process of the present invention, chlorine or bromine is preferred, and chlorine represented by a formula (5):

[Chemical Formula 11]

$$Cl_2 \qquad (5)$$

is particularly preferred.

The form of the halogen used in the process of the present invention is not particularly limited, and may be any form as long as the reaction proceeds. Examples of the form of the halogen used in the process of the present invention include a gas, a liquid and a solid.

Particularly, also the form of the chlorine used in the process of the present invention is not particularly limited, and may be any form as long as the reaction proceeds. Examples of the form of the chlorine used in the process of the present invention include a liquid and a gas. Preferred examples of the form of the chlorine used in the process of the present invention include a gas. The method for introducing chlorine gas is not limited, and, for example, the method for introducing chlorine gas may be any of blowing into the gas phase of the reaction system, or blowing into the liquid phase of the reaction system (e.g., bubbling). Furthermore, when chlorine gas is blown into the liquid phase, an apparatus in which fine bubbles of chlorine gas are generated, or the like may be used. For example, when chlorine gas is blown into the liquid phase of the reaction system, the chlorine gas can be blown therein through a nozzle; the chlorine gas can be blown therein in the form of fine bubbles through a porous element provided at the end of a nozzle; a pipe having numerous holes can be provided in the reaction vessel so that the chlorine gas is blown out of the numerous small holes on the pipe forming bubbles of an appropriately small size; or other various apparatus measures can be taken. In addition, the chlorine gas may be diluted with a gas other than chlorine gas. Examples of the gas used for the dilution of the chlorine gas include, but are not limited to, inert gases such as nitrogen and argon. From the viewpoints of availability, ease of handling, safety, price, etc., nitrogen is preferred. The gas(es) used for the dilution of the chlorine gas may be used singly or as a mixture thereof in any ratio.

The amount of the halogen used in the process of the present invention may be any amount as long as the reaction proceeds. From the viewpoints of yield and/or the suppression of by-products, economic efficiency, etc., the range of 1 mol or more and 60 mol or less, preferably 2 mol or more and 20 mol or less, more preferably 2 mol or more and 10 mol or less, further preferably 2 mol or more and 7 mol or less, and particularly preferably 2 mol or more and 5 mol or less of the halogen represented by the general formula (2), particularly the chlorine represented by the formula (5), based on 1 mol of the nitrile compound represented by the general formula (1), can be mentioned as examples. However, the amount of the halogen used in the process of the present invention can be adjusted appropriately by a person skilled in the art in accordance with the purpose and the situation.

(Operation: Introduction of Halogen)

In the process of the present invention, it is preferred that the nitrile compound, sulfur and the halogen are allowed to react simultaneously with each other. Particularly, in the process of the present invention, it is preferred that succinonitrile, sulfur, and chlorine are allowed to react simultaneously with each other. Therefore, in the process of the present invention, it is preferred to introduce the halogen represented by the general formula (2) into the nitrile compound represented by the general formula (1) and sulfur. Specifically, it is preferred to charge the nitrile compound represented by the general formula (1) and sulfur, and then introduce the halogen represented by the general formula (2) therein. It is possible to charge the total amount of the nitrile compound and the total amount of sulfur, and then introduce the total amount of the halogen. Or it is possible to charge a part of the nitrile compound and a part of sulfur, and then introduce a part of halogen, and then charge the remaining nitrile compound and the remaining sulfur, and then introduce the remaining halogen. Furthermore, the charge of the nitrile compound and sulfur and the introduction of the halogen may be repeated. In these cases, the respective amounts of the nitrile compound and sulfur charged at one time can be adjusted appropriately by a person skilled in the art. The amount of chlorine introduced at one time can also be adjusted appropriately by a person skilled in the art. As long as the reaction proceeds, the methods of these charge and introduction may be selected and adjusted appropriately by a person skilled in the art.

(Molten State)

"Melt" means that a substance becomes liquefied by heating. A "molten state" is a state in which a substance is melted. In the present invention, the nitrile compound represented by the general formula (1) and sulfur are heated, and then, the reaction between the nitrile compound represented by the general formula (1), the sulfur and the halogen represented by the general formula (2) is carried out. Preferably, the nitrile compound represented by the general formula (1) and sulfur are heated until at least either one of the nitrile compound represented by the general formula (1) or the sulfur melts. More preferably, the nitrile compound represented by the general formula (1) and sulfur are heated until at least the nitrile compound represented by the general formula (1) melts. Further preferably, the nitrile compound represented by the general formula (1) and sulfur are heated until at least the nitrile compound represented by the general formula (1) and a part of the sulfur melt. Particularly preferably, the nitrile compound represented by the general formula (1) and sulfur are heated until the nitrile compound represented by the general formula (1) and the sulfur melt.

Specifically, preferably, the halogen represented by the general formula (2) is introduced into a system in which at least either one of the nitrile compound represented by the general formula (1) or sulfur is melted. More preferably, the halogen represented by the general formula (2) is introduced into a system in which at least the nitrile compound represented by the general formula (1) is melted. That is, it is more preferred that the reaction between the nitrile compound represented by the general formula (1), sulfur and the halogen represented by the general formula (2) is carried out by introducing the halogen represented by the general formula (2) into the nitrile compound represented by the general formula (1) in a molten state, and sulfur. Specifically, further preferably, the halogen represented by the general formula (2) is introduced into a system in which at least the nitrile compound represented by the general formula (1) and a part of sulfur are melted. Particularly preferably, the halogen represented by the general formula (2) is introduced into a system in which both the nitrile compound represented by the general formula (1) and sulfur are melted. That is, it is particularly preferred that the reaction between the nitrile compound represented by the general formula (1), sulfur and the halogen represented by the general formula (2) is carried out by introducing the halogen represented by the general formula (2) into the nitrile compound represented by the general formula (1) in a molten state and sulfur in a molten state. In the case where a part of the nitrile compound and a part of sulfur are charged, and then a part of halogen is introduced, and then remaining nitrile compound and the remaining sulfur are charged, and then the remaining halogen is introduced, the state of the nitrile compound and the sulfur may be any of the above molten states when the remaining halogen is introduced.

The above "molten state" is achieved and maintained by heating the nitrile compound represented by the general formula (1) and sulfur. This heating temperature is generally 70° C. or more, preferably 90° C. or more, and is in the range of 70 to 180° C., preferably in the range of 90 to 150° C., taking the upper limit of the heating temperature into consideration, though depending on the type of the nitrile compound.

The above reaction is carried out by introducing the halogen represented by the general formula (2) into a system in which the state of the nitrile compound represented by the general formula (1) and sulfur is any of the above molten states, and therefore, a solvent such as an aprotic polar solvent is not required. That is, the above reaction is carried out without a solvent. However, the addition of an appropriate solvent in a range in which the nitrile compound and the sulfur can be substantially maintained in a molten state is not excluded. The term "without a solvent" referred to herein means that no solvent is added to the reaction system. In other words, the term "without a solvent" referred to herein means that the reaction is carried out in the absence of a solvent. A "solvent" referred to herein is a substance recognized as a "solvent" by a person skilled in the art. For example, the "solvent" referred to herein may be any substance which is a liquid at the reaction temperature. However, the "solvent" does not include a substrate, a reaction intermediate, a reaction product, or a reaction by-product.

An aprotic solvent referred to herein is a solvent having an acceptor number of 24.0 or less. A polar solvent referred to herein is a solvent having a relative dielectric constant of 5 or more. Therefore, an aprotic polar solvent referred to herein is a solvent having an acceptor number of 24.0 or less and a relative dielectric constant of 5 or more. Examples of the aprotic polar solvent include, but are not limited to, N,N-dimethylformamide, N,N-diethylformamide, N,N-dimethylacetamide (DMAC), N,N-diethylacetamide, N-methylpyrrolidone (NMP), tetramethylurea, 1,3-dimethyl-2-imidazolidinone (DMI) hexamethylphosphoric triamide (HMPA) and the like.

The acceptor number (AN) is disclosed in V. Gutmann (translated by Hitoshi Ohtaki and Isao Okada), "Dona To Akuseputa (Donor and Acceptor) (original title: The Donor-Acceptor Approach to Molecular Interaction)", Japan Scientific Societies Press, 1983, or Christian Reichardt, "Solvents and Solvent Effects in Organic Chemistry", 2nd edition, VCH (RFA), 1990, pp. 23-24, or 3rd, updated and enlarged edition, WILEY-VCH, 2003, p. 26, or the like. The acceptor number (AN) is a measure of the acceptor property proposed by Mayer-Gutmann. When the $^{31}$P-NMR chemical shift value of $(C_2F_5)_3PO$ dissolved in n-hexane is set to 0 (zero), and the $^{31}$P-NMR chemical shift value of a $(C_2F_5)_3PO.SbCl_5$ complex in 1,2-dichloroethane is set to 100, the acceptor number (AN) is defined as the $^{31}$P-NMR chemical shift value of $(C_2F_5)_3PO$ dissolved in a certain pure solvent. That is, the acceptor number (AN) of a certain solvent is represented by the following formula; AN=100δ $((C_2F_5)_3PO$ in a certain solvent)/[δ $((C_2F_5)_3PO.SbCl_5$ in 1,2-dichloroethane)−δ $((C_2F_5)_3PO$ in n-hexane)]

Here, the relative dielectric constant is regarded as a value disclosed in "Kagaku Binran (Kisohen) (Handbook of Chemistry (Fundamentals Volume))", edited by the Chemical Society of Japan, Maruzen Co., Ltd., revised 5th edition, 2004, pp. I-770-777.

(Temperature)

The temperature of the reaction between the nitrile compound represented by the general formula (1), the sulfur and the halogen represented by the general formula (2) in the process of the present invention is not particularly limited as long as the reaction proceeds. From the viewpoints of yield and/or the suppression of by-products, operability, economic efficiency, etc., as the reaction temperature in the process of the present invention, 50° C. or more, preferably 70° C. or more, more preferably 80° C. or more, and further preferably 90° C. or more can be mentioned as examples. As the reaction temperature in the process of the present invention, from the same viewpoints, 200° C. or less, preferably 180° C. or less, more preferably 160° C. or less, and further preferably 150° C. or less can be mentioned as examples. As the range of the reaction temperature in the process of the present invention, a range determined by an arbitrary combination of upper limits and lower limits described above can be mentioned as examples. For example, a range determined by a combination of the preferred upper limit and the preferred lower limit described above is preferred, a range determined by a combination of the more preferred upper limit and the more preferred lower limit described above is more preferred, and a range determined by a combination of the further preferred upper limit and the further preferred lower limit described above is further preferred. Specifically, the range of 50 to 200° C., preferably 70 to 180° C., more preferably 80 to 160° C., and further preferably 90 to 150° C. can be mentioned as examples, but the range of the reaction temperature in the process of the present invention is not limited to these. The reaction temperature in the process of the present invention can be adjusted appropriately by a person skilled in the art in accordance with the purpose and the situation.

(Time)

The time of the introduction of the halogen and the reaction time in the process of the present invention is not particularly limited as long as the reaction proceeds. From the viewpoints of yield and/or the suppression of by-products, economic efficiency, etc., particularly from the viewpoint of improvement in yield, as the lower limit of the time in the process of the present invention, 5 hours or more, preferably hours or more, more preferably 15 hours or more, and further preferably 20 hours or more can be mentioned as examples. In addition, the time in the process of the present invention is not particularly limited, and also from the viewpoints of the suppression of the decomposition of the target compound, etc., and a general economic viewpoint, 100 hours or less, preferably 75 hours or less, more preferably 50 hours or less, and further preferably 30 hours or less can be mentioned as examples. As the range of the time in the process of the present invention, any appropriate combination of a lower limit and an upper limit which are described above can be mentioned as examples. The range of 5 to 100 hours, preferably 15 to 100 hours, more preferably 15 to 75 hours, and further preferably 20 to 50 hours, and particularly preferably 20 to 30 hours can be mentioned as examples, but the time in the process of the present invention is not limited to these. The time in the process of the present invention can be adjusted appropriately by a person skilled in the art in accordance with the purpose and the situation. The possibility is suggested that the time of the introduction of the halogen, particularly chlorine, and the reaction time in the process of the present invention are substantially the same.

(Isothiazole Compound)

Specific examples of the isothiazole compound represented by the general formula (3) obtained by the process of the present invention include, but are not limited to,
3,4-difluoro-5-cyanoisothiazole,
3,4-dichloro-5-cyanoisothiazole,
3,4-dibromo-5-cyanoisothiazole,
3,4-diiodo-5-cyanoisothiazole,
3,4-difluoro-5-carboxyisothiazole,
3,4-dichloro-5-carboxyisothiazole,
3,4-dibromo-5-carboxyisothiazole,
3,4-diiodo-5-carboxyisothiazole,
3,4-difluoro-5-methoxycarbonylisothiazole,
3,4-dichloro-5-methoxycarbonylisothiazole,
3,4-dibromo-5-methoxycarbonylisothiazole,
3,4-diiodo-5-methoxycarbonylisothiazole,
3,4-dichloro-5-ethoxycarbonylisothiazole,
3,4-dibromo-5-ethoxycarbonylisothiazole,
3,4-dichloro-5-propoxycarbonylisothiazole,
3,4-dichloro-5-isopropoxycarbonylisothiazole and
3,4-dichloro-5-butoxyisothiazole.

From the viewpoints of the usefulness of the compound, etc., 3,4-dichloro-5-cyanoisothiazole and 3,4-dibromo-5-cyanoisothiazole are preferred, and 3,4-dichloro-5-cyanoisothiazole is particularly preferred.

EXAMPLES

Next, the process of the present invention will be specifically described with reference to Examples; however, the present invention is not limited in any way by these Examples.

Example 1

Production of 3,4-Dichloro-5-cyanoisothiazole

In a 200 ml four-necked flask equipped with a stirrer, a reflux condenser and a thermometer, 80.1 g (1.0 mol) of succinonitrile and 32.1 g (1.0 mol) of sulfur were charged. The temperature was raised to 120° C. under stirring. It was observed that the succinonitrile and the sulfur melted. Therein was blown 212.7 g (3.0 mol) of chlorine at 120 to 125° C. for 22 hours. The reaction mixture was cooled to room temperature, and diluted with 300 ml of ethyl acetate. The insolubles were removed by filtration to obtain the product as a brown ethyl acetate solution. The obtained ethyl acetate solution was analyzed by an HPLC absolute calibration curve method. As a result, the yield of 3,4-dichloro-5-cyanoisothiazole was 64% with respect to the theoretical amount calculated from the amount of the succinonitrile used.

When the process of International Publication No. WO2010/126170 (Patent Document 6) was carried out, the sublimation of a compound presumed to be fumaronitrile, maleonitrile and/or a chlorine-substituted compound thereof was observed. However, in Example 1 of the present specification, the sublimation of a compound was not substantially observed.

The reaction mechanism and the like in the present invention were not clear, but from the above observation, it was presumed that the main reaction mechanism in the present invention was different from the main reaction mechanism in the process of International Publication No. WO2010/126170 (Patent Document 6).

Example 2

Production of 3,4-Dichloro-5-cyanoisothiazole

After a reaction was carried out in the same manner as Example 1, the reaction mixture was cooled to 60° C., and isopropanol (2-propanol) (200 ml) was added dropwise thereto. After the completion of the dropwise addition, the mixture was cooled to 5° C. The crystals were collected by filtration and dried to obtain 3,4-dichloro-5-cyanoisothiazole as pale brown crystals with a yield of 54%. The obtained 3,4-dichloro-5-cyanoisothiazole was a known compound, and was identified in the usual manner known to a person skilled in the art. In addition, the filtrate was analyzed by an HPLC absolute calibration curve method. As a result, the yield of 3,4-dichloro-5-cyanoisothiazole in the filtrate was 10%. The combined yield of the 3,4-dichloro-5-cyanoisothiazole obtained as crystals and the 3,4-dichloro-5-cyanoisothiazole in the filtrate was 64%. Both yields are based on the succinonitrile used as a raw material.

Example 3

Production of 3,4-Dichloro-5-cyanoisothiazole

In a 200 ml four-necked flask equipped with a stirrer, a reflux condenser and a thermometer, 80.1 g (1.0 mol) of succinonitrile and 64.1 g (2.0 mol) of sulfur were charged. The temperature was raised to 100° C. under stirring. It was observed that the succinonitrile melted. It was observed that most of the sulfur remained as a solid. Therein was blown 283.6 g (4.0 mol) of chlorine at 100 to 105° C. for 21 hours. The reaction mixture was cooled to room temperature, and diluted with 300 ml of ethyl acetate. The insolubles were removed by filtration to obtain the product as a brown ethyl acetate solution. The obtained ethyl acetate solution was analyzed by an HPLC absolute calibration curve method. As a result, the yield of 3,4-dichloro-5-cyanoisothiazole was 71% with respect to the theoretical amount calculated from the amount of the succinonitrile used.

Example 4

Production of 3,4-Dichloro-5-cyanoisothiazole

In a 500 ml four-necked flask equipped with a stirrer, a reflux condenser and a thermometer, 80.1 g (1.0 mol) of succinonitrile and 96.2 g (3.0 mol) of sulfur were charged. The temperature was raised to 120° C. under stirring. It was observed that the succinonitrile and the sulfur melted. Therein was blown 283.6 g (4.0 mol) of chlorine at 120 to 125° C. for 12 hours. The reaction mixture was cooled to room temperature, and diluted with 300 ml of ethyl acetate. The insolubles were removed by filtration to obtain the product as a brown ethyl acetate solution. The obtained ethyl acetate solution was analyzed by an HPLC absolute calibration curve method. As a result, the yield of 3,4-dichloro-5-cyanoisothiazole was 68% with respect to the theoretical amount calculated from the amount of the succinonitrile used.

Example 5

Production of 3,4-Dichloro-5-cyanoisothiazole

In a 500 ml four-necked flask equipped with a stirrer, a reflux condenser and a thermometer, 80.1 g (1.0 mol) of succinonitrile and 96.2 g (3.0 mol) of sulfur were charged. The temperature was raised to 120° C. under stirring. It was observed that the succinonitrile and the sulfur melted. Therein was blown 290.7 g (4.1 mol) of chlorine at 120 to 125° C. for 22 hours. The reaction mixture was cooled to room temperature, and diluted with 300 ml of ethyl acetate. The insolubles were removed by filtration to obtain the product as a brown ethyl acetate solution. The obtained ethyl acetate solution was analyzed by an HPLC absolute calibration curve method. As a result, the yield of 3,4-dichloro-5-cyanoisothiazole was 76% with respect to the theoretical amount calculated from the amount of the succinonitrile used.

Example 6

Production of 3,4-Dichloro-5-cyanoisothiazole

In a 200 ml four-necked flask equipped with a stirrer, a reflux condenser and a thermometer, 80.1 g (1.0 mol) of succinonitrile and 32.1 g (1.0 mol) of sulfur were charged. The temperature was raised to 120° C. under stirring. It was observed that the succinonitrile and the sulfur melted. Therein was blown 212.7 g (3.0 mol) of chlorine at 120 to 125° C. for 12 hours. The reaction mixture was cooled to room temperature, and diluted with 300 ml of ethyl acetate. The insolubles were removed by filtration to obtain the product as a brown ethyl acetate solution. The obtained ethyl acetate solution was analyzed by an HPLC absolute calibration curve method. As a result, the yield of 3,4-dichloro-5-cyanoisothiazole was 56% with respect to the theoretical amount calculated from the amount of the succinonitrile used.

Example 7

Production of 3,4-Dichloro-5-cyanoisothiazole

In a 1000 ml four-necked flask equipped with a stirrer, reflux condenser and a thermometer, 80.1 g (1.0 mol) of succinonitrile and 320.7 g (10.0 mol) of sulfur were charged. The temperature was raised to 120° C. under stirring. It was observed that the succinonitrile and the sulfur melted. Therein was blown 581.4 g (8.2 mol) of chlorine at 120 to 125° C. for 16 hours. The reaction mixture was cooled to room temperature, and diluted with 300 ml of ethyl acetate. The insolubles were removed by filtration to obtain the product as a brown ethyl acetate solution. The obtained ethyl acetate solution was analyzed by an HPLC absolute calibration curve method. As a result, the yield of 3,4-dichloro-5-cyanoisothiazole was 75% with respect to the theoretical amount calculated from the amount of the succinonitrile used.

Example 8

Production of 3,4-Dichloro-5-cyanoisothiazole

In a 200 ml four-necked flask equipped with a stirrer, a reflux condenser and a thermometer, 80.1 g (1.0 mol) of succinonitrile and 32.1 g (1.0 mol) of sulfur were charged. The temperature was raised to 140° C. under stirring. It was observed that the succinonitrile and the sulfur melted. Therein was blown 198.5 g (2.8 mol) of chlorine at the same temperature for 18 hours. The reaction mixture was cooled to room temperature, and diluted with 300 ml of ethyl acetate. The insolubles were removed by filtration to obtain the product as a brown ethyl acetate solution. The obtained ethyl acetate solution was analyzed by an HPLC absolute calibration curve method. As a result, the yield of 3,4-dichloro-5-cyanoisothiazole was 63% with respect to the theoretical amount calculated from the amount of the succinonitrile used.

Comparative Example 1

Process Described in Example 2 of Japanese Patent Application Laid-Open No. 2010-260805 (JP 2010-260805 A) (Patent Document 7)

Production of 3,4-Dichloro-5-cyanoisothiazole

In a 300 ml four-necked flask equipped with a stirrer, a reflux condenser and a thermometer, 5.70 g (71.0 mmol) of succinonitrile, 35.5 ml of N,N-dimethylformamide and 36.5 g (1.14 mol) of sulfur were charged. Therein was blown 40.4 g (0.570 mol) of chlorine at 25° C. or less under stirring. Then, the temperature was raised to 100° C., and the mixture was stirred for 6 hours. The reaction mixture was allowed to cool to 25° C., and then poured into ice water. The reaction product was extracted with toluene. The obtained toluene solution was analyzed by an HPLC absolute calibration curve method. As a result, the yield of 3,4-dichloro-5-cyanoisothiazole was 64% with respect to the theoretical amount calculated from the amount of the succinonitrile used.

In Comparative Example 1 of the present specification which is the process described in Example 2 of Japanese Patent Application Laid-Open No. 2010-260805 (JP 2010-260805 A) (Patent Document 7), chlorine and N,N-dimethylformamide are used. Therefore, as described earlier, the process of Comparative Example 1 is different from the present invention which does not require the use of N,N-dimethylformamide, and is not industrially preferred.

It was presumed that in the above Comparative Example 1, sulfur chloride was produced from the chlorine and the sulfur in the system at a low temperature of 25° C. or less, and then the succinonitrile reacted with the sulfur chloride prepared in the system, as described in claims 1 and 6 and the paragraph 0029 of Japanese Patent Application Laid-Open No. 2010-260805 (JP 2010-260805 A) (Patent Document 7).

Meanwhile, as described already, the reaction mechanism and the like in the present invention are not clear. However, when the present invention was discussed after the present invention was completed, it was presumed that the main reaction mechanism in the present invention was different from the main reaction mechanism in the above Comparative Example 1. This is supported also by Comparative Example 2 of the present specification described later.

Comparative Example 2

Process Described in Example 2 of Japanese Patent Application Laid-Open No. 2010-260805 (JP 2010-260805 A) (Patent Document 7) Conducted without Solvent Production of 3,4-Dichloro-5-cyanoisothiazole In a 100 ml eggplant-shaped flask equipped with a stirrer, a reflux condenser and a thermometer, 5.00 g (62.4 mmol) of succinonitrile and 31.9 g (1.0 mol) of sulfur were charged. It was observed that the succinonitrile and the sulfur did not melt. Therein was blown 35.4 g (0.500 mol) of chlorine at 25° C. or less under stirring for 22 hours. Then, the temperature was raised to 100° C., and the mixture was stirred for 6 hours. The reaction mixture was cooled to room temperature, and diluted with 50 ml of toluene. The insolubles were removed by filtration to obtain the product as a brown toluene solution. The obtained toluene solution was analyzed by a GC absolute calibration curve method. As a result, the yield of 3,4-dichloro-5-cyanoisothiazole was only 10% with respect to the theoretical amount calculated from the amount of the succinonitrile used.

In the above Comparative Example 2, the process described in Example 2 of Japanese Patent Application Laid-Open No. 2010-260805 (JP 2010-260805 A) (Patent Document 7) was conducted without using N,N-dimethylformamide which is an aprotic polar solvent, in other words, without a solvent. As a result, the yield decreased significantly.

(High-Performance Liquid Chromatography (HPLC) Analysis Method)

Regarding the details of the above-described HPLC analysis method, the following literatures can be referred to, if necessary.

(a): The Chemical Society of Japan ed., "Shin Jikken kagaku Koza (New Experimental Chemistry Course) 9 Bunseki kagaku (Analytical Chemistry) II", pages 86 to 112 (1977), published by Shingo Iizumi, Maruzen Co., Ltd. (For example, regarding combinations of packing materials and mobile phases that can be used in a column, pages 93 to 96 can be referred to.)

(b): The Chemical Society of Japan ed., "Jikken kagaku Koza (Experimental Chemistry Course) 20-1 Bunseki kagaku (Analytical Chemistry)", 5th ed., pages 130 to 151 (2007), published by Seishiro Murata, Maruzen Co., Ltd. (For example, regarding the specific usage and conditions of reversed phase chromatography analysis, pages 135 to 137 can be referred to.)

(Gas Chromatography (GC) Analysis Method)

Regarding the details of the above-described GC analysis method, the following literatures can be referred to, if necessary.

(a): The Chemical Society of Japan ed., "Shin Jikken kagaku Koza (New Experimental Chemistry Course) 9 Bunseki kagaku (Analytical Chemistry) II", pages 60 to 86 (1977), published by Shingo Iizumi, Maruzen Co., Ltd. (For example, regarding liquids for a stationary phase that can be used in a column, page 66 can be referred to.)

(b): The Chemical Society of Japan ed., "Jikken kagaku Koza (Experimental Chemistry Course) 20-1 Bunseki kagaku (Analytical Chemistry)", 5th ed., pages 121 to 129 (2007), published by Seishiro Murata, Maruzen Co., Ltd. (For example, regarding the specific usage of a hollow capillary separation column, pages 124 to 125 can be referred to.)

According to the process of the present invention, a novel industrial process for producing an isothiazole compound, particularly 3,4-dichloro-5-cyanoisothiazole, is provided. The isothiazole compound which can be produced by the process of the present invention is useful as an intermediate for pharmaceuticals and an intermediate for agricultural chemicals, and an intermediate for functional pigments, electronic materials, etc. Particularly, 3,4-dichloro-5-cyanoisothiazole is useful as an important intermediate for agricultural chemicals.

As described earlier in this specification, the process of the present invention is industrially preferred. For example, the process of the present invention is dramatically safer compared with prior art, and is efficient. Furthermore, in the process of the present invention, it is also possible to select various options in industrial implementation as required. In other words, according to the present invention, economically preferred conditions in accordance with the situation are provided. Therefore, the process of the present invention can be implemented on an industrial scale and in a simple manner. Besides, according to the process of the present invention, the target compound can be produced without using an expensive catalyst and a transition metal, and therefore, harmful waste derived from them is not discharged. Therefore, in the process of the present invention, waste disposal is easy, and the process of the present invention is also environmentally friendly.

Therefore, the process of the present invention is extremely useful as an industrial production process.

The invention claimed is:

1. A process for producing an isothiazole compound represented by a general formula (3):

(3)

wherein R is a cyano group, a carboxy group or an alkoxycarbonyl group; and X is a fluorine atom, a chlorine atom, a bromine atom or an iodine atom,
which comprises heating a nitrile compound represented by a general formula (1):

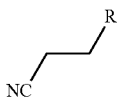

(1)

wherein R is as defined above,
and sulfur, and then carrying out a reaction between the nitrile compound represented by the general formula (1), the sulfur and a halogen represented by a general formula (2):

$X_2$ (2)

wherein X is as defined above.

2. The process according to claim 1, wherein the nitrile compound represented by the general formula (1) and the sulfur are heated until at least the nitrile compound represented by the general formula (1) is melted.

3. The process according to claim 1, wherein the nitrile compound represented by the general formula (1) and the sulfur are heated until the nitrile compound represented by the general formula (1) and the sulfur are melted.

4. The process according to claim 1, wherein the nitrile compound represented by the general formula (1) and the sulfur are heated to 70° C. or more.

5. The process according to claim 1, wherein the nitrile compound represented by the general formula (1) and the sulfur are heated to 90° C. or more.

6. The process according to claim 1, wherein the nitrile compound represented by the general formula (1) and the sulfur are heated to a temperature in the range of 70 to 180° C.

7. The process according to claim 1, wherein the nitrile compound represented by the general formula (1) and the sulfur are heated to a temperature in the range of 90 to 150° C.

8. The process according to claim 1, wherein the reaction between the nitrile compound represented by the general formula (1), the sulfur and the halogen represented by the general formula (2) is carried out at 70° C. or more.

9. The process according to claim 1, wherein the reaction between the nitrile compound represented by the general formula (1), the sulfur and the halogen represented by the general formula (2) is carried out at 90° C. or more.

10. The process according to claim 1, wherein the reaction between the nitrile compound represented by the general formula (1), the sulfur and the halogen represented by the general formula (2) is carried out at a temperature in the range of 70 to 180° C.

11. The process according to claim 1, wherein the reaction between the nitrile compound represented by the general formula (1), the sulfur and the halogen represented by the general formula (2) is carried out at a temperature in the range of 90 to 150° C.

12. The process according to claim 1, wherein the reaction between the nitrile compound represented by the general formula (1), the sulfur and the halogen represented by the general formula (2) is carried out for 15 hours or more.

13. The process according to claim 1, wherein the reaction between the nitrile compound represented by the general formula (1), the sulfur and the halogen represented by the general formula (2) is carried out for 20 hours or more.

14. The process according to claim 1, wherein the reaction between the nitrile compound represented by the general formula (1), the sulfur and the halogen represented by the general formula (2) is carried out for a time period in the range of 15 to 75 hours.

15. The process according to claim 1, wherein the reaction between the nitrile compound represented by the general formula (1), the sulfur and the halogen represented by the general formula (2) is carried out for a time period in the range of 20 to 50 hours.

16. The process according to claim 1, wherein the reaction between the nitrile compound represented by the general formula (1), the sulfur and the halogen represented by the general formula (2) is carried out at a temperature in the range of 70 to 180° C. for a time period in the range of 15 to 75 hours.

17. The process according to claim 1, wherein the reaction between the nitrile compound represented by the general formula (1), the sulfur and the halogen represented by the general formula (2) is carried out at a temperature in the range of 90 to 150° C. for a time period in the range of 15 to 75 hours.

18. The process according to claim 1, wherein the reaction between the nitrile compound represented by the general formula (1), the sulfur and the halogen represented by the general formula (2) is carried out at a temperature in the range of 90 to 150° C. for a time period in the range of 20 to 50 hours.

19. The process according to claim 1, wherein the reaction between the nitrile compound represented by the general formula (1), the sulfur and the halogen represented by the general formula (2) is carried out by charging the nitrile compound represented by the general formula (1) and the sulfur, and then introducing the halogen represented by the general formula (2) therein.

20. The process according to claim 1, wherein the reaction between the nitrile compound represented by the general formula (1), the sulfur and the halogen represented by the general formula (2) is carried out by introducing the halogen represented by the general formula (2) into the nitrile compound represented by the general formula (1) and the sulfur.

21. The process according to claim 1, wherein the reaction between the nitrile compound represented by the general formula (1), the sulfur and the halogen represented by the general formula (2) is carried out by introducing the halogen represented by the general formula (2) into the nitrile compound represented by the general formula (1) in a molten state, and the sulfur.

22. The process according to claim 1, wherein the reaction between the nitrile compound represented by the general formula (1), the sulfur and the halogen represented by the general formula (2) is carried out by introducing the halogen represented by the general formula (2) into the nitrile compound represented by the general formula (1) in a molten state, and the sulfur in a molten state.

23. The process according to claim 1, wherein the reaction between the nitrile compound represented by the general formula (1), the sulfur and the halogen represented by the general formula (2) is carried out at a temperature in the range of 70 to 180° C. for a time period in the range of 15 to 75 hours by introducing the halogen represented by the general formula (2) into the nitrile compound represented by the general formula (1) and the sulfur.

24. The process according to claim 1, wherein the reaction between the nitrile compound represented by the general formula (1), the sulfur and the halogen represented by the general formula (2) is carried out at a temperature in the range of 90 to 150° C. for a time period in the range of 15 to 75 hours by introducing the halogen represented by the general formula (2) into the nitrile compound represented by the general formula (1) and the sulfur.

25. The process according to claim 1, wherein the reaction between the nitrile compound represented by the general formula (1), the sulfur and the halogen represented by the general formula (2) is carried out at a temperature in the range of 90 to 150° C. for a time period in the range of 20 to 50 hours by introducing the halogen represented by the general formula (2) into the nitrile compound represented by the general formula (1) and the sulfur.

26. The process according to claim 1, wherein the reaction between the nitrile compound represented by the general formula (1), the sulfur and the halogen represented by the general formula (2) is carried out without using an aprotic polar solvent.

27. The process according to claim 1, wherein the reaction between the nitrile compound represented by the general formula (1), the sulfur and the halogen represented by the general formula (2) is carried out without a solvent.

28. The process according to claim 1, wherein R in the general formula (1) is a cyano group.

29. The process according to claim 1, wherein X in the general formula (2) is a chlorine atom.

30. The process according to claim 1, wherein R in the general formula (1) is a cyano group, and X in the general formula (2) is a chlorine atom.

* * * * *